United States Patent
Bakker et al.

(10) Patent No.: US 10,166,403 B2
(45) Date of Patent: Jan. 1, 2019

(54) BRACHYTHERAPY SOURCE ASSEMBLY

(75) Inventors: Pier Bakker, Veenendaal (NL); Wim de Jager, Veenendaal (NL); Arie Luite Visscher, Veenendaal (NL); Henk Vreeken, Veenendaal (NL)

(73) Assignee: Nuvletron Operations B.V., Veenendaal (NL)

( * ) Notice: Subject to any disclaimer, the term of this patent is extended or adjusted under 35 U.S.C. 154(b) by 100 days.

(21) Appl. No.: 14/122,853

(22) PCT Filed: Jun. 1, 2012

(86) PCT No.: PCT/NL2012/050386
§ 371 (c)(1),
(2), (4) Date: Jan. 15, 2014

(87) PCT Pub. No.: WO2012/165964
PCT Pub. Date: Dec. 6, 2012

(65) Prior Publication Data
US 2014/0187849 A1   Jul. 3, 2014

(30) Foreign Application Priority Data
Jun. 1, 2011 (NL) .................................... 2006886

(51) Int. Cl.
*A61N 5/10* (2006.01)

(52) U.S. Cl.
CPC ....... *A61N 5/1007* (2013.01); *Y10T 29/49888* (2015.01)

(58) Field of Classification Search
CPC .......................... A61N 5/1001–5/1029; A61N 2005/1003–2005/1025
USPC .......................................................... 600/7–8
See application file for complete search history.

(56) References Cited

U.S. PATENT DOCUMENTS

| | | | | |
|---|---|---|---|---|
| 4,861,520 A | * | 8/1989 | van't Hooft | A61N 5/1001 252/644 |
| 5,160,318 A | | 11/1992 | Shuler | |
| 5,282,781 A | * | 2/1994 | Liprie | A61N 5/1014 600/3 |
| 5,707,332 A | * | 1/1998 | Weinberger | A61N 5/1002 600/3 |

(Continued)

FOREIGN PATENT DOCUMENTS

| EP | 1 346 751 A2 | 9/2003 |
|---|---|---|
| JP | H 05-503303 | 6/1993 |

(Continued)

OTHER PUBLICATIONS

Response to Rule 161 Communication in European Patent Application No. 12729753.9, dated Mar. 21, 2014 (4 pages).

(Continued)

*Primary Examiner* — Catherine B Kuhlman
(74) *Attorney, Agent, or Firm* — Bookoff McAndrews, PLLC

(57) ABSTRACT

An embodiment of the present disclosure is directed to a brachytherapy source assembly including a guiding wire and a brachytherapy capsule located at a distal end of the guiding wire. The capsule includes a chamber defined by a wall for holding a radioactive source. At least a portion of an exterior surface of the wall of the capsule includes at least one of a friction-reducing coating, a wear-resistant coating, and a wear-indication coating a coating.

20 Claims, 1 Drawing Sheet

(56) References Cited

U.S. PATENT DOCUMENTS

Figure 1:
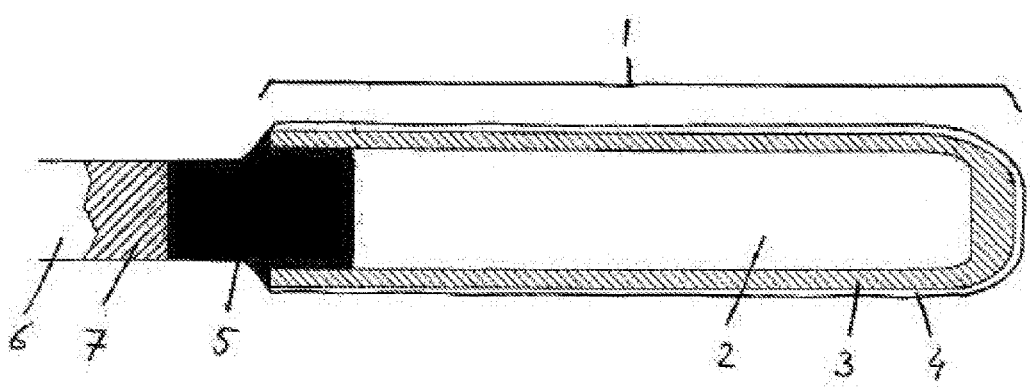

| | | | | |
|---|---|---|---|---|
| 6,099,457 | A | * | 8/2000 | Good .................. A61K 51/1241 600/8 |
| 6,179,768 | B1 | * | 1/2001 | Loffler .................. A61N 5/1002 600/7 |
| 6,352,500 | B1 | * | 3/2002 | Halpern ............... A61N 5/1027 600/3 |
| 6,520,923 | B1 | * | 2/2003 | Jalisi .................. A61M 25/0043 600/585 |
| 6,569,076 | B1 | | 5/2003 | Larsen et al. |
| 2005/0101826 | A1 | * | 5/2005 | Bray ....................... A61L 31/18 600/8 |
| 2005/0165472 | A1 | * | 7/2005 | Glocker ............... A61L 31/088 623/1.15 |
| 2006/0058568 | A1 | * | 3/2006 | Gross .................. A61N 5/1027 600/3 |
| 2009/0246126 | A1 | | 10/2009 | Shani |
| 2009/0318746 | A1 | * | 12/2009 | Thurmond, II ....... A61L 29/041 600/8 |

FOREIGN PATENT DOCUMENTS

| | | |
|---|---|---|
| JP | 2000514328 | 10/2000 |
| JP | 2007-510496 | 4/2007 |
| WO | WO 92/03179 | 3/1992 |
| WO | WO 98/01186 | 1/1998 |
| WO | WO 2005/051454 | 6/2005 |
| WO | WO 2011/053908 A1 | 5/2011 |
| WO | WO 2012/165964 | 12/2012 |

OTHER PUBLICATIONS

Office Action issued in European Patent Application No. 12729753.9, dated Mar. 20, 2015 (6 pages).

Reply to Office Action filed in European Patent Application No. 12729753.9, dated Jul. 17, 2015 (9 pages).

Summons to Attend Oral Proceedings issued in European Patent Application No. 12729753.9, dated Nov. 12, 2015 (7 pages).

International Search Search Report relating to PCT/NL2012/050386 dated Nov. 23, 2012, 5 pages.

* cited by examiner

BRACHYTHERAPY SOURCE ASSEMBLY

CROSS-REFERENCE TO RELATED APPLICATIONS

This application is a national phase application of International Application No. PCT/NL2012/050386, filed on Jun. 1, 2012, which claims the benefit of priority of NL Application No. 2006886, filed on Jun. 1, 2011. Each of these applications is herein incorporated by reference in their entireties.

The invention is directed to a brachytherapy source assembly, to a kit of parts, to a method for preparing a brachytherapy source assembly, to the uses of a specific coating on a capsule, and to a brachytherapy treatment.

Brachytherapy is a key cornerstone of cancer care. Unlike external beam radiation therapy (EBRT) which delivers an external radiation source through healthy tissue, brachytherapy delivers the radioactive dose directly within or adjacent to the tumour. A capsule with a radioactive source is delivered, via a hollow needle, a flexible tube or a catheter or the like, to the area to be treated. Normally, for this purpose the so-called afterloading technique is employed, according to which the catheter, or the like, is first placed in the body and then the capsule containing the radioactive source and attached to the distal end of a push/pull wire (also referred to as guiding wire, i.e. to guide the radioactive source through the hollow needle, flexible tube or catheter) is delivered with the help of a remotely controlled device to the treatment area. Computer-controlled remote afterloading devices position one or more small radioactive sources, whose activity works over very short distances, within specially designed applicators to be delivered to the target area, with high precision. This allows a tailored radiation dose to be precisely delivered to the target area, while minimising unwanted exposure of the surrounding healthy tissues and organs. Furthermore, the very nature of the physics of brachytherapy helps minimise exposure to healthy tissues. Brachytherapy depends on the "inverse square law"; around a source of radiation, the dose falls off at the square of the distance. Thus, the tissues around the treated tumour receive a much lower dose than anticipated by other radiation methods.

Brachytherapy combines two fundamental aims of radiotherapy: an effective tumour dose with sparing of the surrounding tissue. Advanced computerised treatment planning and image-guided delivery systems increase efficiencies and improve outcomes and patient acceptability. It achieves this through the placement of a radioactive source within or adjacent to a tumour using specially designed applicators and remote, computer-controlled delivery devices. This allows a tailored radiation dose to be delivered very precisely to the target area, while minimising unwanted exposure of the surrounding healthy tissues and organs. Experience and insight gained in extensive clinical research and widespread clinical practice demonstrate the following key advantages of brachytherapy.

Brachytherapy is used worldwide to treat a wide range of cancers and other diseases. Brachytherapy is the standard treatment for cervical cancer and an important part of treatment guidelines for others including prostate, breast, skin, and head and neck cancers, but also other body cancer positions.

The ability of brachytherapy to deliver high radiation doses over a short time period means patients can complete treatment in days rather than the weeks required for EBRT. For example, high dose-rate (HDR) brachytherapy treatment for prostate cancer can be delivered in two treatment sessions, compared to several weeks with EBRT. This has important potential implications for patient compliance with their radiotherapy treatment, as well as minimising impact on patients' lives.

Brachytherapy is generally well tolerated with a good toxicity profile for many of its applications, largely due to its tissue sparing approach. Adverse events are similar or better than other treatment modalities in the case of cervical, prostate and breast cancers. In prostate cancer, for example, the use of brachytherapy results in lower longer term issues with bowel, bladder and erectile function.

As pressure on healthcare resources intensifies, reductions in the overall length of treatment and increased use of outpatient-based treatment as seen in brachytherapy are effective ways to reduce costs and provide more efficient use of resources. Additionally, brachytherapy involves lower overall infrastructure costs than newer forms of EBRT, such as proton therapy, and provides the opportunity to maximise existing resources in a radiotherapy department (e.g. reducing congestion on linear accelerator use).

Brachytherapy can be characterised according to the dose rate used: low, medium or high. The ability of brachytherapy to deliver high radiation doses over a short period of time is important for treatment efficacy, as both the total radiation dose and the rate at which it is delivered affect destruction of the cancer cells. More cancerous cells are destroyed when a treatment dose is administered over a short time frame, and HDR brachytherapy achieves a similar overall effect as EBRT, especially to the surrounding non-cancerous tissue. A shorter course of therapy may also offer better tumour control as cells have a decreased opportunity to repopulate between treatments. Rapid dose decline of the radioactive source increases with distance from the tumour site, and results in decreased toxicity to healthy surrounding tissues.

For efficient treatment using an afterloader, the combination of the capsule and push/pull wire should have a high degree of flexibility to be able to follow the curves of the catheter. Even when the catheter is forming sharp curves, it should be possible to move the capsule through the catheter without much friction and without causing wear to the capsule. If the capsule experiences a considerable amount of friction when being moved through the catheter and positioned at the tumour location then this could lead to a decrease in positioning accuracy. Since the therapy will be most effective when the capsule is positioned accurately at the pre-determined tumour site (most tumour cells killed and least healthy tissue damaged), the positioning accuracy is of high importance to the outcome of the applied therapy. In addition, wear of the capsule could (in the extreme) lead to capsule leakage, and a radioactive spill and/or exposure. This kind of leakage could lead to contamination of the afterloading system, or worse contact with the patient, which is a serious safety risk. Therefore, it is desirable to have a brachytherapy source assembly with high wear resistance thereby ensuring the integrity of the capsule wall. Furthermore, it would be advantageous to be able to detect any wear of the capsule over time.

An objective of the invention is to provide a brachytherapy source assembly, having a high integrity of the capsule wall.

A further objective of the invention is to provide a brachytherapy source assembly that can be positioned using an afterloading device with high accuracy.

Yet a further objective of the invention is to provide a detection mechanism for detecting wear of a capsule in a brachytherapy system.

It has been found that these objectives can, at least in part, be met by providing a brachytherapy assembly, wherein the capsule has a special type of coating.

Accordingly, in a first aspect the invention is directed to a brachytherapy source assembly, comprising a push/pull wire and at the distal end thereof a capsule suitable for brachytherapy, wherein said capsule comprises a chamber for holding one or more radioactive sources, said chamber being defined by a wall, and wherein at least part of the exterior surface of the wall of the capsule comprises a coating, the coating comprising one or more selected from TiN, TiCN, TiCrN, CrN, TiAlCrN, diamond-like carbon (DLC), $MoS_2$, or other suitable coating material, wherein said capsule is attached to the push/pull wire or wherein said capsule is comprised in the push/pull wire.

It was found that in accordance with the invention the capsule has improved integrity due to the physical properties of the specific coating material. In addition, the brachytherapy source assembly of the invention can be positioned with an afterloading device with high accuracy of about 0.1-1 mm, such 0.5-1 mm due to the relatively low friction coefficient of the capsule. Accordingly, the brachytherapy source assembly can be pushed smoothly back and forth through a catheter. In addition, it was found that in some embodiments of the present invention, the coating can serve as a wear indicator. If the coating has a different colour from the underlying capsule wall, then a change in colour can indicate that the capsule has been subject to wear and should be replaced.

The capsule in the brachytherapy source assembly of the invention may be used for low dose-rate brachytherapy, medium dose-rate brachytherapy, high dose-rate brachytherapy, or pulsed dose-rate brachytherapy. Since the above-indicated problems of positioning accuracy and capsule integrity are especially pronounced for high dose-rate brachytherapy where the source activity is relatively high and the dangers of leakage or inaccuracy are higher, the capsule for brachytherapy is in a preferred embodiment a capsule for high dose-rate brachytherapy.

The term "low dose-rate" as used in this application is meant to refer to dose-rates in the range of 0.4 $Gy \cdot hr^{-1}$ to 2 $Gy \cdot hr^{-1}$.

The term "medium dose-rate" as used in this application is meant to refer to dose-rates in the range of 2 $Gy \cdot hr^{-1}$ to 12 $Gy \cdot hr^{-1}$.

The term "high dose-rate" as used in this application is meant to refer to dose-rates of greater than 12 $Gy \cdot hr^{-1}$ (0.2 $Gy \cdot min^{-1}$). In practice, most HDR machines operate at even higher dose-rates, typically about 2 $Gy \cdot min^{-1}$. In HDR brachytherapy, a high intensity (about 3 to 30 curie) radiation source is used and it is typically inserted into the tumour and moved through a series of pre-planned and pre-determined dwell positions, each dwell position being held for a maximum of a few seconds, typically the time the source is in the patient is less than 30 minutes per fraction. HDR brachytherapy is currently inter alia applied in treatments of prostate, breast, cervix, uterus, lung, eye and other anatomical sites.

The term "pulsed dose-rate" as used in this application is meant to refer to the technique where high dose-rate pulses of treatment (typically lasting five or ten minutes) are repeated at short intervals (typically once per hour). The intention is to simulate the radiobiological effects of low dose-rate treatment using a high dose-rate type machine. Clinicians who prefer the radiobiological effects of LDR can achieve this but with the flexibility of the complex dose distributions achievable by a modern HDR machine.

The term "diamond-like carbon" (DLC) as used in this application is meant to refer to a carbonaceous structure with both $sp^2$ and $sp^3$ hybridised bonds in an amorphous form. Diamond-like carbon has an amorphous matrix of carbon atoms or a mixture of carbon and hydrogen atoms very largely linked in a tetrahedral structure like carbon in diamond. DLC is mostly metastable amorphous material but can include a microcrystalline phase. Examples of DLC include amorphous diamond (a-D), amorphous carbon (a-C), tetrahedral amorphous carbon (ta-C) and diamond-like hydrocarbon and the like. Ta—C is the most preferred DLC.

The term "radioactive source" as used in this application is meant to refer to a radioactive source in any kind of form, including in the form of a pellet, a powder, and a coating.

The capsule in the brachytherapy source assembly of the invention comprises a chamber for holding a radioactive source. The chamber can be a closed chamber. The chamber of the capsule is defined by a wall which surrounds the chamber. Typically, the wall is a cylindrical mantle that is closed at the distal end of the capsule (defined as the end of the capsule which is intended to be inserted into the patient first). The wall may be made of a biologically inert material. However, this is not critical, because the capsule is almost always surrounded by an applicator (medical instrument) or catheter and therefore and therefore normally does not come into direct contact with body fluids or tissue. The distal end of the capsule may have a semi-spherical shape in order to be guided through the catheter with low friction. The length of the capsule can be in the range of 2-10 mm, such as in the range of 2.5-8 mm, or in the range of 3-6 mm. The width (or cross section diameter) of the capsule may be in the range of 0.4-2 mm, such as in the range of 0.5-1.5 mm, or in the range of 0.6-1.2 mm. The proximal end of the capsule (defined as the end of the capsule which is intended to be inserted into the patient last) can be sealed, such as with a plug. Preferably, the chamber for holding the radioactive source is closed by this seal. The seal is typically accomplished by welding, such as laser welding.

The chamber is intended to hold a radioactive source. However, the chamber may also be empty. Such an "empty" capsule is frequently used at the start of a brachytherapy treatment. The "empty" capsule can be driven in and out of the catheter to check the positioning of the capsule and to check whether any obstructions are present in the path through the catheter or applicator. After having performed this initial check, a capsule containing radioactive material can be driven into the catheter in order to carry out the actual treatment. The empty chamber preferably comprises void space. In case the chamber comprises a radioactive source, this radioactive source is normally present in the chamber in the form of a pellet. Usually, the radioactive source does not completely fill the chamber and accordingly also the chamber which is filled with the radioactive source comprises void space.

Various radioactive materials may be used in combination with the brachytherapy capsule of the invention. Preferably, the radioactive source is selected from the group consisting of iridium-192 and cobalt-60.

Iridium-192 can be produced by the neutron activation of iridium-191. It has a half-life of 74 days and decays by β-emission as shown in equation (1).

$$_{77}^{192}Ir \rightarrow {_{78}^{192}}Pt + {_{-1}^{0}}e + \gamma \qquad (1)$$

The photon emission is a complex spectrum with a weighted mean of about 0.38 MeV. When freshly produced, iridium-192 is contaminated by small amounts of the radioactive iridium-194, which arises from the neutron activation of stable iridium-193. However, this has a half-life of 17 hours and rapidly decays into insignificance. Iridium-192 has high specific activity permits a high activity source to have small dimensions.

Cobalt-60 can be produced by neutron activation of the stable cobalt-59. It has a half-life of 5.26 years and decays by β-emission as shown in equation (2).

(2)

It emits γ energies of 1.17 and 1.33 MeV.

Other suitable radioactive sources include caesium-137, californium-252, gold-198, indium-114 palladium-103, phosphorus-32, radium-226, ruthenium-106, samarium-145, strontium-90, tantalum-182, thulium-107, tungsten-181, and ytterbium-169.

The material used for the wall of the capsule is preferably corrosion resistant. In an embodiment, the wall comprises one or more materials selected from the group consisting of steel (including stainless steel and austenitic steel), titanium, and nickel. In particular, stainless steel and titanium are considered very suitable materials for the capsule wall. In a further embodiment, the wall of the capsule comprises one or more materials selected from the group consisting of ceramics and composites.

Preferably, the capsule wall has an average thickness in the range of 25-500 μm, preferably in the range of 50-250 μm. If the capsule wall has an average thickness of less than 25 μm thick then the risk of possible leaks increases, whereas wall thicknesses of more than 500 μm give rise to considerable shielding thereby reducing the treatment efficacy.

In accordance with the invention, at least part of the exterior surface of the wall of the capsule comprises a coating. Preferably, the coating is present on the complete exterior surface of the wall of the capsule. Hence, then the exterior surface of the capsule is completely covered with the coating. The coating comprises one or more selected from TiN, TiCN, TiCrN, CrN, TiAlCrN, DLC, and $MoS_2$. In particular, it is preferred that the coating comprises titanium nitride and/or DLC. These materials have an advantageously low friction coefficient, even at small layer thicknesses.

The average coating thickness can be in the range of 1-15 μm, and is preferably in the range of 1-10 μm, such as in the range of 1-5 μm. Coatings with an average thickness in these ranges exhibit excellent properties of friction and wear resistance. Suitable methods for determining the layer thickness include destructive methods (such as by grinding a spherical cap through the layer and base material using an abrasive ball and recalculating the layer thickness by determination of cap diameters and ball diameters) and non-destructive methods (such as X-ray fluorescence).

In an embodiment, the capsule in the brachytherapy source assembly of the invention is provided with a coating that has a friction coefficient in the range of 0.02-0.5. Preferably, the friction coefficient of the coating is in the range of 0.03-0.3. The friction coefficient of a coating can be measured, for instance, in a pin-on-disc installation, where a well defined, coated pin is pressed against a rotating disc made of 100Cr6 steel (under dry or lubricated conditions).

In accordance with a special embodiment of the invention, the wall and the coating material have a different colour, thereby allowing a user to see a difference in colour when the coating is partly removed, such as by wear or damage. This creates a mechanism for detecting wear of the capsule during use. In accordance with this special embodiment, it is preferred that the wall is made of one or more selected from steel, titanium, and nickel, while the coating is made of one or more selected from TiN, TiCN, TiAlCrN, and DLC, Steel, titanium and nickel each have a grey or silver colour. A TiN coating typically has a gold colour; a TiCN coating typically has a blue-grey colour, a TiAlCrN coating typically has an anthracite colour; and a DLC coating typically has a black colour. The colour contrast between these wall and coating materials is therefore such that wear of the capsule can easily be detected.

The difference in colour between the coating material and the base material is easily detected by use of visual inspection or optical means and could be easily automated. Thus any change in the colour of the surface material can be detected and used to provide an indication of any wear on the surface of the capsule. With this information, the capsule can be withdrawn from service before any erosion or wear becomes serious enough to risk a leak of radioactive material or the safety of a patient or operator.

The capsule may be attached to the push/pull wire via a crimp joint, a press joint, a click joint, a weld or a glue (adhesive) joint. Particularly suitable examples for attaching the capsule to the push/pull wire are a weld and/or a coupling sleeve.

The push/pull wire material may be the same as the capsule wall material. In an embodiment, the capsule is comprised in a push/pull wire, for instance by the provision of a chamber within the push/pull wire. In that case, part of the push/pull wire material forms the wall of the chamber of the capsule.

Preferably, the push/pull wire is a thin, flexible wire made of a metal material such as steel or titanium. In a special embodiment, the push/pull wire may also have the form of a rod or tubing.

In another embodiment, the push/pull wire may be in the form of a thin flexible rod made from a titanium alloy such as NiTinol™ and the capsule is formed in a distal end of the push/pull wire, for instance by the drilling or forming of a chamber within the NiTinol™ rod. In that case, part of the push/pull wire material forms the wall of the chamber of the capsule.

In another embodiment, the chamber of the capsule is closed by means of a plug. Preferably, the plug is at the proximal end of the capsule, i.e. the end of the capsule that is attached to the push/pull wire. The plug may be manufactured from an inert metal material, such as titanium or stainless steel. The chamber of the capsule is typically sealed by the welding the plug to the wall.

The push/pull wire can be attached to the capsule by a weld, crimp or alternatively by gluing (such as with epoxy), and/or by using a coupling sleeve. In such cases, part of the surface of said weld, and/or coupling sleeve can comprise the same or a similar coating as the capsule. Also the push/pull wire may comprise the same or a similar coating.

The brachytherapy source assembly of the invention is intended for use in brachytherapy. An international standard for sealed radioactive sources is known as ISO standard 2919:2012. This standard is based on test performance and specifies general requirements, performance tests, production tests, marking and certification.

An example of a brachytherapy capsule assembly of the invention is schematically depicted in FIG. 1. The brachytherapy source assembly shown in FIG. 1 comprises a capsule 1. Capsule 1 has a chamber 2 for holding a radioactive source (not shown). Chamber 2 is defined by a wall 3. At least part of the exterior surface of wall 3 of the capsule comprises a coating 4. As shown in FIG. 1, chamber 2 does not necessarily have to be enclosed completely by wall 3.

Chamber 2 of capsule 1 of the brachytherapy source assembly shown in FIG. 1 is closed by means of plug 5. Capsule 1 is attached to push/pull wire 6 by means of weld 7. In the brachytherapy source assembly shown in FIG. 1 the exterior surface of wall 3 is entirely coated with coating 4. Optionally, coating 4 may also be applied on the exterior surface of plug 5, push/pull wire 6 and/or weld 7.

Figure 2:
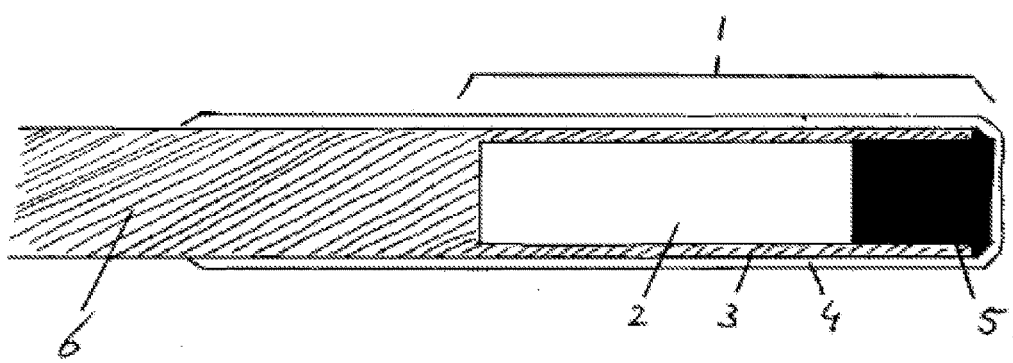

A further example of a brachytherapy source assembly of the invention is schematically depicted in FIG. 2. The brachytherapy assembly shown in FIG. 2 also comprises a capsule 1, having a chamber 2 for holding a radioactive source (not shown). In the example shown in FIG. 2, however, the push/pull wire is in the form of a NiTinol™ rod or flexible material such as a memory metal and the chamber 2 is created by excavating or hollowing out an end portion of the push/pull wire 6. Hence, wall 3 (that defines chamber 2) is part of push/pull wire 6. Alternatively, chamber 2 may be excavated or hollowed out from a material that can subsequently be attached to push/pull wire 6 (such as by a weld). A coating 4 is applied on the exterior surface of wall 3. In the example shown in FIG. 2, coating 4 can also be applied on part of push/pull wire 6 and sleeve assembly 8. In FIG. 2, chamber 2 is closed by plug 5 on the distal side. In the embodiment of FIG. 2, coating 4 is also applied on plug 5.

In a further aspect, the invention is directed to a kit of parts comprising a brachytherapy source assembly as described herein and a catheter, flexible tube or hollow needle for guiding said brachytherapy source assembly to a treatment site.

In accordance with the invention, friction that is caused by moving the brachytherapy source assembly back and forth through the catheter, flexible tube or hollow needle is advantageously reduced. The combination of brachytherapy source assembly and catheter, flexible tube or hollow needle advantageously allows the capsule to be positioned accurately at the treatment site. Additionally, the kit of parts allows the use of non-biocompatible materials for the capsule wall, the coating, and/or the push/pull wire since only the outer surface of the catheter or the like is in direct contact with the body of the patient.

In yet a further aspect, the invention is directed to a method for preparing a brachytherapy source assembly, preferably as described herein, wherein said method comprises the steps of providing a capsule that comprises a chamber for holding a radioactive source, said chamber being defined by a wall, applying to at least part of the exterior surface of the wall of the capsule a coating, wherein the coating comprising one or more selected from TiN, TiCN, TiCrN, CrN, TiAlCrN, DLC, and $MoS_2$, and optionally attaching said capsule to a push/pull wire.

In case the capsule is comprised in the push/pull wire, the step of providing a capsule may comprise excavating or hollowing out an end portion of a push/pull wire. Alternatively, the capsule may be provided separately and be attached to a separate push/pull wire.

The coating may be applied using various deposition techniques known in the art. Suitable techniques include physical vapour deposition (including cathodic arc deposition, electron beam physical vapour deposition, evaporative deposition, pulsed laser deposition, sputter deposition), chemical vapour deposition (including microwave plasma-assisted chemical vapour deposition, plasma-enhanced chemical vapour deposition, remote plasma-enhanced chemical vapour deposition, atomic layer chemical vapour deposition, combustion chemical vapour deposition, hot wire chemical vapour deposition, metalorganic chemical vapour deposition, hybrid physical-chemical vapour deposition, rapid thermal chemical vapour deposition, and vapour phase epitaxy), and deposition welding, such as laser cladding. Preferably, the coating is applied by means of physical vapour deposition, chemical vapour deposition or laser cladding.

In a further aspect, the invention is directed to the use of a coating as described herein on a brachytherapy capsule for decreasing friction and/or wear of the capsule or any other part of the assembly.

In yet a further aspect, the invention is directed to the use of a coating as described herein on a brachytherapy capsule (preferably the capsule in a brachytherapy source assembly comprising a capsule and a push/pull wire, such as described herein) as an indicator for detecting wear. For such use it is preferred that the capsule has a chamber wall made of one or more selected from steel, titanium, and nickel, while the coating is made of one or more selected from TiN, TiCN, TiAlCrN, and DLC.

The use of a coating as described herein for reducing friction and providing a surface wear indication is applicable and relevant for a brachytherapy source assembly containing a radioactive source, as well as for brachytherapy assemblies having "dummy" capsules or "check" capsules used to check and ensure the catheter or applicator path is unobstructed before treatment is commenced with the capsule containing a radiation source.

In yet a further aspect, the invention is directed to a brachytherapy treatment comprising applying to an individual in need thereof, a brachytherapy source assembly as described herein. The brachytherapy treatment may be a high dose-rate brachytherapy treatment or, in a special embodiment, a pulsed dose-rate brachytherapy treatment. In a pulsed dose-rate brachytherapy treatment, high dose-rate pulses of treatment that typically last for a period of five to ten minutes) are repeated at short intervals. The intervals may vary, for instance, from once per 30 minutes to once per 3 hours. Typically, the high dose-rate pulses are repeated once per hour.

Suitably, the brachytherapy source assembly can be applied to the treatment site by feeding the brachytherapy source assembly through a catheter, flexible tube, hollow needle or applicator.

The invention claimed is:

1. A brachytherapy source assembly for delivering high dose-rate (HDR) or pulsed dose-rate (PDR) brachytherapy using a computer-controlled remote afterloading device, the source assembly comprising:

a source device, comprising:
a push/pull wire having a proximal end and a distal end;
a capsule located at a distal end region of the push/pull wire, wherein the capsule includes a chamber at least partially defined by a wall and containing a radioactive source, and wherein a proximal end of the capsule has a diameter that is greater than a diameter of the distal end of the push/pull wire;
a weld attaching the capsule to the push/pull wire;
a plug configured to maintain the radioactive source within the chamber; and
a wear-indication coating covering an exterior surface of the capsule wall, wherein the wear-indication coating has a first color and the exterior surface of the capsule wall has a second color that visibly contrasts the first color of the coating upon visual inspection; and a dummy device, comprising:
  a push/pull wire having a proximal end and a distal end;
  a capsule located at a distal end region of the push/pull wire;
  a weld attaching the capsule to the push/pull wire; and
  a wear-indication coating covering an exterior surface of the capsule, wherein the wear-indication coating has a first color and the exterior surface of the capsule has a second color that visibly contrasts the first color of the coating upon visual inspection;
  wherein the dummy device does not include a radioactive source.

2. The brachytherapy source assembly according to claim 1, wherein the coating on the source device and the coating on the dummy device comprise at least one of the materials selected from the group consisting of TiN, TiCN, TiCrN, CrN, TiAlCrN, DLC, and MoS$_2$.

3. The brachytherapy source assembly according to claim 1, wherein the coating on the source device and the coating on the dummy device have an average thickness in the range of approximately 1-15 micrometers.

4. The brachytherapy source assembly according to claim 1, wherein the coating on the source device and the coating on the dummy device have a friction coefficient in the range of approximately 0.02-0.5.

5. The brachytherapy source assembly according to claim 1, wherein the capsule wall of the source device and the capsule of the dummy device comprise at least one of the materials selected from the group consisting of steel, stainless steel, titanium, nickel, and aluminium.

6. The brachytherapy source assembly according to claim 1, wherein the capsule wall of the source device and the capsule of the dummy device include ceramics.

7. The brachytherapy source assembly according to claim 1, wherein the capsule wall has an average thickness in the range of 25-500 micrometers.

8. The brachytherapy source assembly according to claim 1, wherein the wall of the source device and the capsule of the dummy device are made of at least one of the materials selected from the group consisting of steel, stainless steel, titanium, and nickel, and the coating of the source device and the coating of the dummy device are made of at least one of the materials selected from the group consisting of TiN, TiCN, TiAlCrN, and DLC.

9. The brachytherapy source assembly according to claim 1, wherein the radioactive source is a pellet.

10. The brachytherapy source assembly according to claim 1, wherein the radioactive source includes at least one of the materials selected from the group consisting of iridium-192 and cobalt-60.

11. The brachytherapy source assembly according to claim 1, wherein the capsule of the source device complies with ISO standard 2919:2012.

12. A kit comprising the brachytherapy source assembly according to claim 1, and a delivery device configured to guide the brachytherapy source assembly to a treatment site.

13. The brachytherapy source assembly according to claim 1, wherein the capsule of the source device is configured to removeably receive the radioactive source.

14. The brachytherapy source assembly according to claim 1, wherein the wall of the source device and the capsule of the dummy device are made of stainless steel, wherein the coating of the source device and the coating of the dummy device are made of at least one of the materials selected from the group consisting of TiN, and wherein the radioactive source includes cobalt-60.

15. A method of brachytherapy treatment comprising:
  positioning the brachytherapy source assembly of claim 1 at a treatment site.

16. The brachytherapy treatment method according to claim 15, wherein the brachytherapy source assembly is positioned at the treatment site by passing the brachytherapy source assembly through a delivery device.

17. The brachytherapy treatment method according to claim 15, further comprising visually assessing whether there is a local change in color of the exterior surface of at least one of the capsule for brachytherapy or the capsule for the dummy device as a result of partly wearing away of the wear-indicating coating.

18. A method for preparing a brachytherapy source assembly for delivering high dose-rate (HDR) or pulsed dose-rate (PDR) brachytherapy using a computer-controlled remote afterloading device, the method, comprising:
  providing a capsule for brachytherapy that includes a chamber containing a radioactive source, the chamber being at least partially defined by a wall;
  applying a wear-indication coating to an exterior surface of the wall of the capsule, wherein the wear-indication coating has a first color and the exterior surface of the wall of the capsule has a second color that visibly contrasts the first color of the coating upon visual inspection;
  inserting a plug into the capsule, wherein the plug is configured to maintain the radioactive source within the chamber; and
  welding the capsule to a first push/pull wire, wherein the first push/pull wire is configured to position the capsule for brachytherapy treatment;
  providing a capsule for a dummy device, wherein the capsule for the dummy device does not contain a radioactive source:
  applying the wear-indication coating to an exterior surface of the capsule for the dummy device, wherein the wear-indication coating has a first color and the exterior surface of the capsule for the dummy device has a second color that visibly contrasts the first color of the coating upon visual inspection; and
  welding the capsule for the dummy device to a second push/pull wire, wherein the second push/pull wire is configured to position the capsule for the dummy device.

19. The method according to claim 18, wherein the coating is applied to the exterior surface of the capsule for brachytherapy and the capsule for the dummy device using a technique selected from the group consisting of physical vapour deposition, chemical vapour deposition, and laser cladding.

20. A brachytherapy source assembly comprising:
  a source device, comprising:
    a push/pull wire having a proximal end and a distal end;
    a capsule located at a distal end region of the push/pull wire, wherein the capsule includes a chamber at least partially defined by a wall and containing a radioactive source;
    a weld attaching the capsule to the push/pull wire;
    a plug configured to maintain the radioactive source within the chamber; and
    a wear-indication coating covering the capsule wall, wherein the wear-indication coating has a first color and the exterior surface of the capsule wall has a second color that visibly contrasts the first color of the coating upon visual inspection; and a dummy device, comprising:
  a push/pull wire having a proximal end and a distal end;
  a capsule located at a distal end region of the push/pull wire;
  a weld attaching the capsule to the push/pull wire; and
  a wear-indication coating covering an exterior surface of the capsule, wherein the wear-indication coating has a first color and the exterior surface of the capsule has a second color that visibly contrasts the first color of the coating upon visual inspection;
  wherein the dummy device does not include a radioactive source.

* * * * *

UNITED STATES PATENT AND TRADEMARK OFFICE
CERTIFICATE OF CORRECTION

| | |
|---|---|
| PATENT NO. | : 10,166,403 B2 |
| APPLICATION NO. | : 14/122853 |
| DATED | : January 1, 2019 |
| INVENTOR(S) | : Pier Bakker et al. |

It is certified that error appears in the above-identified patent and that said Letters Patent is hereby corrected as shown below:

On the Title Page

Item (73), delete "Nuvletron" and insert -- Nucletron --.

Signed and Sealed this
Sixteenth Day of April, 2019

Andrei Iancu
*Director of the United States Patent and Trademark Office*